United States Patent
Bendale et al.

(10) Patent No.: US 9,943,544 B2
(45) Date of Patent: Apr. 17, 2018

(54) PROCESS FOR BIO SYNTHESIS OF NANO ARSENIC TRIOXIDE AND ITS USE IN TREATMENT OF DISEASES INCLUDING CANCER

(71) Applicants: Yogesh Narayan Bendale, Pune (IN); Vineeta Yogesh Bendale, Pune (IN)

(72) Inventors: Yogesh Narayan Bendale, Pune (IN); Vineeta Yogesh Bendale, Pune (IN)

(*) Notice: Subject to any disclaimer, the term of this patent is extended or adjusted under 35 U.S.C. 154(b) by 297 days.

(21) Appl. No.: 14/661,529

(22) Filed: Mar. 18, 2015

(65) Prior Publication Data
US 2016/0271177 A1    Sep. 22, 2016

(51) Int. Cl.
*A61K 33/36*    (2006.01)
*C01G 28/00*    (2006.01)

(52) U.S. Cl.
CPC ............ *A61K 33/36* (2013.01); *C01G 28/005* (2013.01)

(58) Field of Classification Search
CPC .................................................. A61K 36/00
See application file for complete search history.

*Primary Examiner* — Qiuwen Mi
(74) *Attorney, Agent, or Firm* — HM Law Group LLP; Vani Moodley, Esq.

(57) ABSTRACT

The present invention is a process for bio synthesis of nano arsenic trioxide defined by its low toxicity, higher bio availability and nano particle size with the aid of buttermilk, goat urine, *dolichos biflorous* and other plant materials such as ginger, *momordica charantia* and *musa paradisiaca*. The invention is carried out in different steps involving purification of crude form of arsenic trioxide by boiling it with buttermilk, goat urine and extract of *dolichos biflorous* in subsequent steps, followed by the trituration of the bio purified arsenic trioxide with extracts of ginger and *momordica charantia* in subsequent steps and heating of the dry product obtained after trituration with *musa paradisiaca* resulting in the production of novel nano arsenic trioxide. The product is effective in the treatment of various diseases including different types of cancer in animals and humans. The product obtained through the process is less toxic with higher bio availability.

3 Claims, No Drawings

PROCESS FOR BIO SYNTHESIS OF NANO ARSENIC TRIOXIDE AND ITS USE IN TREATMENT OF DISEASES INCLUDING CANCER

CROSS REFERENCE TO RELATED APPLICATIONS

This application claims priority of PCT application number PCT/IB2012/054992, filed Sep. 20, 2012.

FIELD OF INVENTION

The present invention is a novel process for production of nano arsenic trioxide with the aid of plant materials, buttermilk and goats urine. The process is environment friendly. The novel product obtained through the present inventive process is more bio available and therapeutically effective in the treatment of various diseases including but not limited to leukemia, other types of malignant and benign tumours, rheumatism. The present inventive product also finds application in agriculture, horticulture, veterinary treatment and other fields where arsenic trioxide can be used as known to people skilled in the art.

BACKGROUND OF INVENTION

Applicability of Arsenic minerals is known in traditional Chinese and Indian medicine since ancient times. In the 18th Century Thomas Fowler compounded a potassium bicarbonate based solution of arsenic trioxide ($As_2O_3$) which came to be known as Fowler's solution. Pharmacology texts of the 18th Century indicate the use of arsenical pastes for the treatment of variety of diseases including cancer [Karen H. Antman; Introduction: The history of arsenic trioxide in cancer therapy; The Oncologist 2001; 6(suppl 2):1-2]. In the 1990's it was reported by the Chinese investigators that herbal mixture containing arsenic trioxide could induce complete remission in patients suffering from acute promyelocytic leukaemia. [Dan Douer, Wendy Hu et. Al.; Arsenic trioxide (Trisenox) Therapy for Acute Promyelocytic Leukaemia in the setting of hematopoietic stem cell transplantation; The Oncologist 2003; 8:132-140].

Arsenic widely exists in nature in its trivalent and pentavalent forms. Arsenic toxicity highly depends on its chemical form. In Indian and Chinese traditional medicines three forms of arsenic minerals i.e., Orpiment, Realgar and Arsenolite, are used alone and also in conjunction with other minerals for treatment of various diseases. The disposition of these arsenicals in the body depends on various key factors, including solubility, absorption, distribution, and excretion. Arsenic trioxide is the most bio available but it is highly toxic compared to Orpiment and Realger. Realgar is also a major component in bhasmas of Indian Ayurvedic medicine. Realger is used both for external as well as internal application. Arsenic trioxide, obtained after purification of Arsenolite, has short term toxicity due to which its therapeutic application is a major concern. To increase the therapeutic application of Realgar, nano particles of Realgar is prepared by cryogrinding with polyvinylpyrrolidone and Sodium Dodecyl Sulphate. (Jie Liu et. al., Mineral Arsenicals in Traditional Medicines:Orpiment, Realger, and Arsenolite, The Journal of Pharmacology and experimental therapeutics, Vol. 326, No. 2, pg. 363-368, 2008).

Prior art search indicates that arsenic trioxide is and has been used in the treatment of cancer. EP2374463, EP2394702, EP 1562616, WO9924029, U.S. Pat. No. 6,884,439, U.S. Pat. No. 6,855,339, U.S. Pat. No. 6,982,096, U.S. Pat. No. 6,723,351, U.S. Pat. No. 6,720,011 are the results of prior art search indicating use of arsenic trioxide in therapy. However the present invention is unique in terms of the process of preparation and the novel nano arsenic trioxide obtained through the present inventive process is generally of particle size ranging from 10 nm to 1000 nm. Further, the novel product is chemically more stable, bio available and safe due to less toxic nature for therapeutic administration in humans, animals and plants. The prior art process for production of arsenic trioxide that is used for therapeutic application involves purification of arsenic trioxide through chemical process. The present invention purifies arsenic trioxide through bio synthesis.

The present invention relates to the production of novel nano arsenic trioxide by a novel process, which involves purification, making it chemically more stable, and particle size reduction of arsenic trioxide, with plant materials, buttermilk and goat urine. The plant materials used in the present process are *Dolichos biflorous, Momordica charantia, Zingiber officinale, Musa paradisica*. The scope of the invention also include use of the active ingredients found in the herein mentioned plant materials, buttermilk, goat urine or other plant, organic or inorganic materials, containing cellulose, with similar characteristics and chemical properties, as known to the people skilled in the art, for the purpose of inventive process and production of the novel product.

Buttermilk is a fermented dairy product obtained from cow's milk. The tartness of buttermilk is due to the presence of lactic acid. The pH level of buttermilk is generally noted to be 4.41 to 4.84. Butter milk can be made through traditional process, by culturing and also through acidification process of milk. One phase of the invention involves purification of arsenic trioxide with the aid of buttermilk. Use of buttermilk is one embodiment of this invention and it is possible to derive the same results if buttermilk is substituted with any other fermented form of milk either obtained through traditional methods or cultured. The substitution of fermented milk obtained through traditional methods or cultured with that of chemically produced or induced active ingredients with same effect known to people skilled in the art cannot be ruled out.

Goat and Cow urine have been an ingredient in Indian Ayurvedic medicine and other traditional Indian Medicine. Goat Urine is used in treatment of tuberculosis by tribals in Western ghats, India [P. Padmanabhan & amp; K. A. Sujana, 2008, Animal products in traditional medicine from Attapady hills of Western Ghats, Indian Journal of Traditional Medicine, Vol. 7(2), pg. 326-329]. However, the use of the goat urine as in the present process is not traditional knowledge or anticipated.

The medicinal values of plant materials belonging to genus *Zingiber* and family Zingiberaceae is well known in traditional medicines. *Zingiber Officinale* is plant species of genus *Zingiber*. The rhizome of *Zingiber Officinale*, Ginger, is one of the most widely used species of ginger family Zingiberaceae and is known for its medicinal use in traditional Chinese and Indian medicine. Ginger has many active ingredients such as Sesquiterpene hydrocarbons predominantly Zingiberene, active gingerols that can be converted to shogaols, Zingerone, Paradol. 6-Gingerol and 6-shogaols have shown pharmacological activities including anti pyretic, analgesic and in treatment of chemotherapy induced nausea (Monograph, Alternative Medicine Review, Volume 8, No. 3, 2003, pg. 331-335). However, use of ginger or extract of plant material of family of *Zingiber Officinale* for particle size reduction of metalloid is not known. The present inventive process also involve particle size reduction of arsenic trioxide to nano particles with aid of ginger.

*Momordica charantia* (Bitter Melon) is a tropical vegetable of family Cucurbitaceae. It is a flowering vine with known medicinal properties. Its fruits contain glycosides, saponins, alkaloids, reducing sugars, resins, phenolic constituents, fixed oils and free acids. Chemical constituents in *Momordica Charantia* are Alkaloids, charantin, charine, cryptoxanthin, cucurbitins, cucurbitacins, cucurbitanes, cycloartenols, diosgenin, elaeostearic acids, erythrodiol, galacturonic acids, gentisic acid, goyaglycosides, goyasaponins, guanylate cyclise inhibitors, gypsogenin, hydroxytryptamines, karounidiols, lanosterol, lauric acid, linoleic acid, linolenic acid, momorcharasides, momorcharins, momordenol, momordicilin, momordicins, momordicinin, momordicosides, momordin, momordolo, multiflorenol, myristic acid, nerolidol, oleanolic acid, oleic acid, oxalic, acid, pentadecans, peptides, petroselinic acid, polypeptides, proteins, ribosome-inactivating proteins, rosmarinic acid, rubixanthin, spinasterol, steroidal glycosides, stigmasta-diols, stigmasterol, taraxerol, trehalose, trypsin inhibitors, uracil, vacine, v-insulin, verbascoside, vicine, zeatin, zeatin riboside, zeaxanthin, zeinoxanthin Amino acids-aspartic acid, serine, glutamic acid, thscinne, alanine, g-amino butyric acid and pipecolic acid, ascorbigen, b-sitosterol-d-glucoside, citrulline, elasterol, flavochrome, lutein, lycopene, pipecolic acid.

*Musa paradisica* is a herbaceous plant of the genus *Musa*. The older scientific name *Musa paradisica* is seldom used due to the advent of hybrid varieties. Presently the species are referred to as *Musa acuminata* or *Musa balbisiana* or triploid hybrids. The fruit as well as the plant materials have medicinal value. In the present invention the extract of the plant material is used.

*Dolichos biflorous* is commonly used as an astringent, diuretic and tonic. The enzymes found in *Dolichos biflorous* have been identified as Urease, Allantoinase, Ribonuclease, Nicotinamide deaminase, b-n-acetylglucosaminidase, a and b galactosidase, a-mannosidase and b glucosidase.

SUMMARY OF THE INVENTION

To increase the therapeutic applicability and bio availability of arsenic trioxide, the present invention purifies, through bio purification, arsenic trioxide available in the market by the process of boiling, trituration, and heating, with plant materials, buttermilk and goats urine. In short, the arsenic trioxide in its crude form as available in the market is put through process of purification by boiling with buttermilk, Goat urine and *Dolichos biflorous* in consecutive steps. Thus purified arsenic trioxide is put through particle size reduction by process of trituration with extract of plant material of taxonomical genus *Momordica* and extract of rizhome of taxonomical genus *Zingiber*. The product obtained from trituration is then heated with extract of plant material of genus *Musa*. The process of heating is carried out in a container with closed lid so as to collect the sublimed product. The product collected from the inner side of the lid of the container is the novel nano arsenic trioxide with high therapeutic value and solubility. Further, bioavailability and therapeutic applicability of the novel product, nano arsenic trioxide, obtained through this inventive process is higher due to its less toxic nature and particle size.

DETAILED DESCRIPTION

Arsenic trioxide, crude powder form, available in the market, is bio purified with the aid of butter milk, Goat urine, and aqueous extract of *Dolichos biflorous* in various steps followed by trituration and heating as detailed below:

Step 1: Arsenic trioxide in coarse powder form is submerged into an earthen vessel containing boiling butter milk. The arsenic trioxide is hung to submerge into the boiling butter milk without touching sides of the earthen vessel. This process is carried out for seven hours. At all times the arsenic trioxide should be submerged during the process of boiling. Hence, buttermilk will have to be added repeatedly during the process of boiling to maintain arsenic trioxide in submerged condition throughout the period.

Step 2: After boiling arsenic trioxide with butter milk in accordance with step 1, the same is hung and submerged into boiling goat urine contained in an earthen vessel, without touching the sides of the container. This process is carried out for seven hours. During this step too arsenic trioxide is to be retained submerged through the whole period of boiling with goat urine and hence it would be required to add goat urine during the process to maintain the arsenic trioxide in submerged condition.

Step 3: After boiling arsenic trioxide with goat urine in accordance with step 2, the same is then hung and submerged, into boiling aqueous extract of *Dolichos biflorous* contained in an earthen vessel, without touching the sides of the container. This process is carried out for 7 hours. Similar to the earlier steps, addition of aqueous extract of *Dolichos biflorous* repeatedly is required throughout the period of boiling to maintain the arsenic trioxide completely submerged.

The time of seven hours for the process continuation provided in step 1 to 3 cannot be considered as limiting. In the process arsenic trioxide can be hung using a cotton string or with materials of similar characteristic. The vessel used can be an earthen container or any vessel with similar characteristics that may be known to persons skilled in the art. Product is yellowish white powder. Biological variation that may occur in goat urine, buttermilk, and the extract of plant materials is anticipated in the present invention. The scope of the present invention also anticipates the use of buttermilk, goat urine and extract of *dolichos* biflorous in interchangable order, as in similar result is possible if the Arsenic Trioxide is put through step 1, 2 or 3 in different orders where by step 3 or step 2 can be performed as step 1 or vice versa.

Step 4: The product of Step 3 is triturated with extract of *Momordica charantia* for 7 hours. The time for trituration cannot be considered limiting. The process of trituration is repeated thrice consecutively, i.e., once the product of trituration is completely dry then the next trituration should be commenced with. Generally it takes 7 hours for the mixture to dry out but 7 hours cannot be considered limiting, as the number of hours depends upon the quantity of the material.

Step 5: The product of Step 4 is triturated with extract of ginger, rhizome of *Zingiber officinale* for 7 hours. The time for trituration cannot be considered limiting. Similar to Step 4, the trituration is carried out thrice consecutively whereby the dry product obtained after trituration is further triturated with extract of rhizome of *Zinziber Officianale* until dry.

The time provided for trituration i.e., seven hours cannot be considered limiting and the desired result can be obtained if the trituration is carried out for less or more hours. The particle size of the product would vary with the number of hours of trituration. The possibility of obtaining the desired result if the trituration is carried out with a mixture of the plant materials or its active ingredients, specified in steps 4 and 5, or other organic or inorganic materials with similar characteristics, is within the scope of this invention. The resultant product is generally yellowish white in colour.

Step 6: The product of Step 5 is heated with extract of the stem of *Musa paradisica* in a closed earthen container with removable lid, volume ratio of the product and extract of the stem of *Musa paradisica* is preferably 1:10. The heating is gradual and carried out for 12 hours. The heating duration cannot be considered limiting. The sublimated product on the inner side of the lid of the container is the final product. The final product is generally white in colour with mild yellow tinge. The maximum temperature to which the present process is subjected to is approximately 500 degree centigrade. However, the desirable result can be obtained at below or above 500 degree centigrade and hence the temperature of heating cannot be considered as limiting. The temperature at which the product is obtained would vary with the quantity of the crude arsenic trioxide and other ingredients.

The container or apparatus for carrying out the present process is an earthen vessel with a removable lid or any other vessel, which is known to the people skilled in the art to bring about similar results.

The ingredients in the steps mentioned above are one embodiment of the invention. The scope of the invention also include active ingredients of the plant and other materials used in the process, organic as well as inorganic, or other plant materials and organic or inorganic materials with similar characteristics or chemical properties, containing cellulose, that are known to people skilled in the art to bring desired effects on substitution of buttermilk, Goat Urine, *Dolichos biflorous*, *Momordica Charantia*, Ginger, *Musa Paradisica* or other aids in this novel process for production of nano arsenic trioxide.

The administration of this chemically more stable, novel nano arsenic trioxide obtained through this inventive process can be done as is or in combination with other minerals, metals, chemical elements or compounds. Both in vitro and in vivo administration is possible with this novel nano arsenic trioxide. The oral administration of the product can be in conjunction with honey or water or any other suitable carrier. The dosage of administration can range from 0.01 mg per kg body weight to 10 mg per kg body weight. It can be administered on daily basis depending on the nature of the disease. In case of cancer the period of administration can be until complete remission or reduction of tumour as the case may be.

The dosage form can be in powder, tablet, capsule, caplet, effervescent, fluid, gelatinous, granules or in any other palatable and administrable form.

The nano arsenic trioxide obtained through this process, generally of size varying from 10 nm to 1000 nm, can also be used in nutraceutical, herbal and mineral composition apart from pharmaceutical or other therapeutic composition.

The product of the present inventive process is also effective in treatment of cancers which are malignant and benign, haematological malignancies such as Promyelocytic Leukemia, other types of Leukemias, Lymphomas, solid tumours like Lung Cancers, Liver cancers etc. The application of this Nano Arsenic Trioxide is not only limited to various cancers but also includes other degenerative and metabolic disorders of vital organs such as lungs, liver, brain, kidneys etc. This has wide application in Neurological cancer disorders and also in multiple infective disorders especially but not limiting to antibiotics or anti microbial resistant infections such as Tuberculosis. This novel arsenic trioxide has got specific action on various enzymatic and hormonal activities in the body for treatment of diseases, including but not limited to, Diabetes. It has got specific action on bone developments in general and at epiphyseal level including prevention and cure of bone and other types of cancers. Use of the present novel product in the treatment of animals, plants, herbs or other flora and industrial application in nutraceutical, cosmetic, herbal, mineral and other composition is anticipated.

The following are a few examples. However the examples provided hereunder must not be considered limiting as to the scope, working or use of the present invention:

Examples of Formulation

| Sr. No. | Arsenic Trioxide dose in mg | Weight of lactose monohydrate in mg | Magnesium stearate in mg | Total weight, in mg/ capsule | Actual weight of powder to be filled in mg/capsule |
| --- | --- | --- | --- | --- | --- |
| 1 | 6 | 57.00 | 0.5 | 63.50 | 64* |
| 2 | 12 | 56.00 | 0.5 | 68.50 | 69* |

What is claimed is:

1. The process comprising the steps of:
preparing a first product by submerging and boiling crude powder form of arsenic trioxide subsequently in each of the following: buttermilk, Goat urine and aqueous extract of *dolichos biflorus;*
performing a first trituration of the prepared first product with an extract of *Momordica charantia* until dry;
performing a second trituration of the dry product produced after the first trituration with extract of ginger until dry; and
heating a resultant product obtained after the second trituration with an extract of *Musa paradisiaca* in an apparatus with a lid and collecting a resultant sublimed product comprising nano arsenic trioxide, from an inner side of the lid.

2. The process of claim 1, wherein the resultant sublimed product obtained is palatable and administrable.

3. The product of the process of claim 1.

* * * * *